United States Patent
Ritz et al.

(10) Patent No.: US 10,639,328 B1
(45) Date of Patent: May 5, 2020

(54) COMPOSITIONS AND METHODS FOR REDUCING HYPERGLYCEMIA AND TREATING DIABETES

(71) Applicants: College of William & Mary, Williamsburg, VA (US); Auxulin Pharmaceuticals Inc, Chesterland, OH (US)

(72) Inventors: Thomas Ritz, Chesterland, OH (US); Gary Ritz, Chesterland, OH (US); Jason P. McDevitt, Williamsburg, VA (US)

( * ) Notice: Subject to any disclaimer, the term of this patent is extended or adjusted under 35 U.S.C. 154(b) by 0 days.

(21) Appl. No.: 16/428,388

(22) Filed: May 31, 2019

Related U.S. Application Data

(60) Provisional application No. 62/824,439, filed on Mar. 27, 2019.

(51) Int. Cl.
| | | |
|---|---|---|
| *A61K 33/14* | (2006.01) | |
| *A61K 38/28* | (2006.01) | |
| *A61K 9/00* | (2006.01) | |
| *A61P 3/10* | (2006.01) | |
| *A61K 31/194* | (2006.01) | |
| *A61K 31/19* | (2006.01) | |
| *A61K 31/375* | (2006.01) | |

(52) U.S. Cl.
CPC ............ *A61K 33/14* (2013.01); *A61K 9/0053* (2013.01); *A61K 9/0095* (2013.01); *A61K 31/19* (2013.01); *A61K 31/194* (2013.01); *A61K 31/375* (2013.01); *A61K 38/28* (2013.01); *A61P 3/10* (2018.01)

(58) Field of Classification Search
CPC .... A61K 33/14; A61K 31/375; A61K 9/0053; A61K 9/0095; A61K 31/194; A61K 31/19; A61K 38/28; A61P 3/10
See application file for complete search history.

(56) References Cited

U.S. PATENT DOCUMENTS

| | | | |
|---|---|---|---|
| 2014/0227202 A1* | 8/2014 | Pilgaonkar | A61K 8/0216 424/52 |
| 2016/0166695 A1* | 6/2016 | Akers | A61K 47/12 514/5.9 |

OTHER PUBLICATIONS

Akturk et al., "Possible Ways to Improve Postprandial Glucose Control in Type 1 Diabetes", Diabetes Technology & Therapeutics (2018), pp. 24-32, vol. 20 (supplement 2).
Hardern et al., "Emergency management of diabetic ketoacidosis in adults", Emerg. Med. J. (2003), pp. 210-213, vol. 20.
American Diabetes Association, "Hyperglycemic Crises in Patients With Diabetes Mellitus", Diabetes Care (2003), pp. s109-s117, vol. 26 (supplement 1).
Provenzano et al., "Dietary Sodium Intake in Type 2 Diabetes", Clin. Diabetes (2014), pp. 106-112, vol. 32.
Inzucchi et al., "Management of Hyperglycemia in Type 2 Diabetes: A Patient-Centered Approach: Position Statement of the American Diabetes Association (ADA) and the European Association for the Study of Diabetes (EASD)" (2012), pp. 1364-1379, vol. 35.

\* cited by examiner

*Primary Examiner* — Robert S Cabral
(74) *Attorney, Agent, or Firm* — Jason P. McDevitt

(57) ABSTRACT

The disclosure describes methods and compositions for reducing the duration of hyperglycemia and treating diabetes and complications thereof. A human subject with hyperglycemia is administered insulin, a water-based beverage, and a sodium salt formulation sufficient to accelerate said subject's return to a non-hyperglycemic state. This process can be repeated multiple times within a given time period.

21 Claims, 1 Drawing Sheet

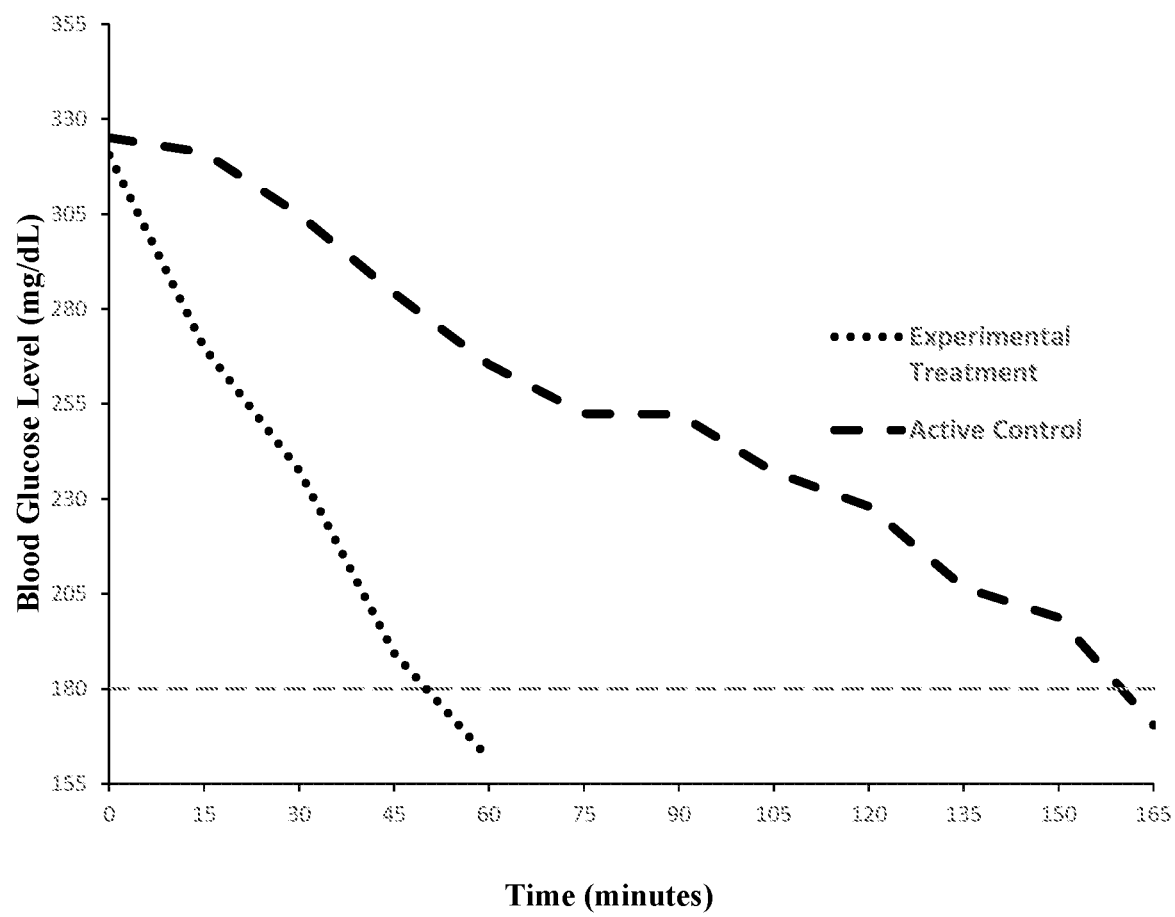

COMPOSITIONS AND METHODS FOR REDUCING HYPERGLYCEMIA AND TREATING DIABETES

STATEMENT REGARDING FEDERALLY SPONSORED RESEARCH OR DEVELOPMENT

The present application claims priority under 35 U.S.C. § 119(e) to U.S. Provisional Patent Application No. 62/824,439, filed Mar. 27, 2019, the entire disclosure of which is incorporated by reference herein.

CROSS-REFERENCE TO RELATED APPLICATIONS

Not Applicable

BACKGROUND

Field

The field of the disclosure relates to methods and pharmaceutical compositions for reducing hyperglycemia and treating diabetes.

Description of Related Art

Glucose is the primary provider of energy for the normal functions of the human body. Glucose supports the functions of both the brain and red blood cells. The body involuntarily will elevate blood sugar in response to low blood sugar (hypoglycemia) in two fashions. Glucose is stored by the liver, as glycogen, and is converted back to glucose through a process known as glycogenolysis. The liver will also fabricate glucose in a process known as gluconeogenesis. High blood sugar is known as hyperglycemia. The pancreas of a non-diabetic person will involuntarily secrete insulin based on blood glucose level and the amount of carbohydrates ingested. This prevents the onset of hyperglycemia. Therefore, glucose and insulin work in tandem to regulate the body's blood sugar level so that the body can carry out its normal functions. The regulation of high and low blood sugars for diabetics is the primary challenge for the management of diabetes. Type 1 diabetics are unable to produce insulin, and therefore must use external sources of insulin at specific time intervals to manage both their body's normal functions and to allow them to consume carbohydrates and fats. Type 2 diabetics make insulin, but do not process it properly. According to the American Diabetes Association, in 2015 there were roughly 30 million Americans with diabetes, of which approximately 1.25 million were Type 1 diabetics.

The consumption of carbohydrates and administration of insulin is a precarious balancing act for a Type 1 diabetic, with the ultimate goal being a blood sugar level between 70-130 mg/dl. Management of proper blood sugar levels is difficult to achieve and typically entails a strict regimen including proper diet, regular exercise, carbohydrate counting, frequent blood sugar monitoring, regular injections of insulin, and other factors specific to each individual. For a Type 1 diabetic, injectable insulin is the primary means of lowering blood sugar level. Many Type 1 diabetics use a basal-bolus regimen, wherein basal insulin (comprising either intermediate insulin or long-acting insulin) is administered once or twice a day to provide steady release of insulin throughout the day. Bolus insulin (comprising short-acting or rapid-acting insulin) is administered in conjunction with meals to keep blood glucose levels under control after a meal. Note that insulin pumps can use shorter-acting insulin to provide a basal insulin function (as well as bolus insulin function) by providing insulin throughout the day.

Hypoglycemia has a variety of dangerous effects on a diabetic's health. A hypoglycemic blood sugar level varies from person to person, and is often defined as any level less than 70 mg/dl. Hypoglycemia is treated with high amounts of short-acting, high-sugar carbohydrates. There are also numerous nutraceuticals and pharmaceuticals commercially available for treating hypoglycemia. These include: pills, gels, liquids, powders, and injectables. Correction of a low blood sugar can take anywhere between 15 to 30 minutes.

Hyperglycemia is defined herein as a blood sugar level greater than 180 mg/dL. A significantly hyperglycemic blood sugar level is defined herein as a blood sugar level greater than 250 mg/dL. Short term effects include: fatigue, headache, blurred vision, diabetic ketoacidosis, and reduced insulin effectiveness. Long term effects include: cardiovascular disease, nerve damage, kidney damage, retinopathy, higher risk of infection, and memory loss. Unlike low blood sugar, a Type 1 diabetic has only one interventional option for treatment of high blood sugar, which is taking insulin. The correction of a high blood sugar level typically takes several hours. Generally, a Type 1 diabetic experiencing a hyperglycemic state will take a short-acting insulin correction, drink water, and wait for their blood sugar to normalize. This process can take several hours, and a diabetic will typically continue to administer insulin until their blood sugar returns to a normal range. If a diabetic subject's blood sugar remains hyperglycemic for too long, the diabetic subject can develop ketoacidosis and be hospitalized and placed on an IV regiment, often for a period of 24 hours. The cost of this treatment can exceed $10,000.

Intracellular sodium plays a vital role in lowering blood sugar levels and preventing diabetic ketoacidosis. When a person's blood sugar is within a normal range, that person's potassium-sodium pump moves glucose out of the blood vessels and into the body. However, when a diabetic's blood sugar level rises and he/she become hyperglycemic, the levels of sodium within the arteries can drop significantly. Hyperglycemia can put a diabetic subject at risk of developing diabetic ketoacidosis (DKA), which is the most common cause of hospitalization for Type 1 diabetics and has an associated mortality risk. DKA occurs when the body is unable to utilize glucose, and it requires an alternative energy source to function. This alternative energy source is fat, which when broken down and used for energy, releases keto acids. The release of keto acids can cause dangerous complications due to the potential significant drop in blood pH levels, and can also cause a diabetic subject to be resistant to insulin that is injected.

The medium-term cumulative effects of hyperglycemia can be approximated by the hemoglobin A1C test, also referred to as A1C or glycated hemoglobin. Glucose attaches to hemoglobin in blood cells, and the higher the glucose level in the blood, the more glucose will attach to hemoglobin. The A1C test measures the amount of hemoglobin having attached glucose and is proportional to average blood glucose levels over the preceding three months. According to the National Institute of Diabetes and Digestive and Kidney Diseases (NIDDK) within NIH, the A1C test is the primary test used for diabetes management, normal A1C levels are below 5.7%, and people with diabetes typically have A1C levels above 6.5%. Type 1 diabetics often have high A1C levels because they frequently become hyperglycemic and do not quickly return to a normal blood sugar level.

Relative to the rest of the population, Type 1 diabetics can have a lower quality of life due to a much higher risk of conditions such as retinopathy, kidney damage, neuropathy, and cardiovascular issues. NIDDK funded the landmark Diabetes Control and Complications Trial (DCCT, see https://www.niddk.nih.gov/about-niddk/research-areas/diabetes/blood-glucose-control-studies-type-1-diabetes-dcct-edic) to determine if people with Type 1 diabetes who kept their blood glucose levels as close to normal as reasonably possible with intensive treatment could slow the development of eye, kidney, and nerve disease, compared with people who used conventional treatment at the time of the study. The study ended after 10 years in 1993, and showed that people who used intensive treatment substantially lowered their A1C levels (to 7% versus 9% in the conventional treatment group) and lowered their risk of diabetic eye disease by 76 percent, diabetic kidney disease by 50 percent, and diabetic nerve disease by 60 percent.

A follow-up to the DCCT known as the EDIC study continued to follow participants in the DCCT study for over 20 years (see Jacobson, A., Braffett, B., Cleary, P., Gubitosi-Klug, R., & Larkin, M. (2013). The Long-Term Effects of Type 1 Diabetes Treatment and Complications on Health-Related Quality of Life: A 23-year follow-up of the Diabetes Control and Complications/Epidemiology of Diabetes Interventions and Complications Cohort. Diabetes Care, 36(10), 3131-3138. doi: 10.2337/dc12-2109). The EDIC study showed that early and intensive blood glucose control during the DCCT substantially lowered the risk over the following 20 years of cardiovascular disease and related deaths, eye surgery for diabetic disease, kidney disease, and nerve problems. The significant reduction in diabetic complications occurred even though the control and treatment groups had similar blood glucose levels and average A1C percentages for the period after the DCCT study ended. Importantly, DCCT participants in the treatment group (tight, aggressive management of blood glucose) lived longer than participants in the conventional treatment group.

Prolonged periods of hyperglycemia can be harmful to health, both in the short-term and long-term. Nevertheless, Type 1 diabetics still spend significant periods of time in hyperglycemic states, and have insufficient means to accelerate the return of blood sugar levels to sub-hyperglycemic states. There is a clinical need for methods and compositions useful for augmenting control of hyperglycemia for diabetics which are disclosed herein.

SUMMARY

This disclosure relates to methods and pharmaceutical compositions for reducing the duration of hyperglycemia in hyperglycemic human beings. In some embodiments, this disclosure provides a method comprising administering to a hyperglycemic human being at least one dose of a therapeutically effective dose of a sodium salt, wherein the blood glucose level of said human being decreases to a sub-hyperglycemic level within about 90 minutes, optionally within about 75 minutes or about 60 minutes or about 45 minutes, after administration of the therapeutically effective dose. In some embodiments, methods for reducing the duration of hyperglycemia comprise the sequential steps of (i) testing (or having tested) the blood glucose level of a human subject to determine if the subject's starting blood glucose level is hyperglycemic; and (ii) if said testing indicates that said subject's starting blood glucose level is hyperglycemic, administering to said subject a dose of insulin and a sufficient dose of a sodium salt such that said subject's ending blood glucose level drops to sub-hyperglycemic levels within 75 minutes of administering said sodium salt, wherein said sodium salt is administered at a dose of sodium between 10 mg sodium per kg and 100 mg sodium per kg body weight of said subject.

The insulin dosage administered in conjunction with the sodium salt can be any safe amount of insulin and is typically the amount of insulin recommended for administration in the situation. Either the sodium salt or the insulin can be administered first, but they are administered within 30 minutes of each other, preferably within 15 minutes of each other, and more preferably within five minutes of each other.

In preferred embodiments, the human subject has diabetes, either Type 1 diabetes or Type 2 diabetes. In such embodiments, the methods described herein improve the treatment of diabetes. The methods of the disclosure, when used when a diabetic patient is hyperglycemic, are particularly effective in preventing diabetic ketoacidosis, and/or reducing the duration and impact of any such ketoacidosis events. This has the advantage of reducing hospitalizations, costs, and mortality. By reducing the time and magnitude of hyperglycemic episodes, the methods also reduce the unpleasant symptoms of hyperglycemia, sometimes including headache, frequent urination, increased thirst, fatigue, nausea, shortness of breath, and general discomfort. Accordingly, the methods of the disclosure can significantly reduce short-term health complications of diabetes.

Moreover, the methods of the disclosure can significantly reduce the long-term health complications of diabetes. In some embodiments, the sequential steps described above (e.g., (i) testing or having tested the blood glucose level of a human subject to determine if the subject's blood glucose level is hyperglycemic; and (ii) if said testing indicates that said subject's blood glucose level is hyperglycemic, administering to said subject a dose of insulin and a sufficient dose of a sodium salt such that said subject's blood glucose level drops to sub-hyperglycemic levels within 75 minutes of administering said sodium salt, wherein said sodium salt is administered at a dose of sodium between 10 mg sodium per kg and 100 mg sodium per kg body weight of said subject) are repeated multiple times within a year, within three months, within one month, within a week, or even within a day. By repeatedly reducing the duration and magnitude of hyperglycemic episodes, the methods can decrease hemoglobin A1C percentage in a diabetic patient relative to the hemoglobin A1C percentage if the methods described herein were not used, and can reduce long-term health complications associated with diabetes, including retinopathy, kidney damage, neuropathy, or cardiovascular issues, and short lifespans.

These sequential steps should not be repeated more than 10 times in any given week because of safety issues associated with too much intake of sodium and/or counterions. For example, the sequential steps can be repeated at least three times within a three-month period (the typical window covered by hemoglobin A1C percentages), or at least 6 times, or at least 10 times, or at least 20 times, or at least 30 times, or at least 60 times, or at least 90 times within a three-month period. In many typical embodiments, a Type 1 diabetic subject would use the methods at least once and less than 20 times per month, and often between 2 and 15 times per month.

In some embodiments, the sufficient dose of a sodium salt is administered to the individual only if the blood glucose testing indicates that the individual is significantly hyperglycemic, i.e., having a blood glucose level greater than 250 mg/dL. In other embodiments, the threshold for administering the sufficient dose of a sodium salt is a blood glucose level exceeding 275 mg/dL, or exceeding 300 mg/dL, or exceeding 325 mg/dL, or is determined by the diabetic subject or his/her physician.

In some embodiments, the steps of testing a human subject's blood glucose level and administering a sufficient dose of a sodium salt are performed by the subject. In other embodiments, these steps are performed by a caretaker such as a nurse or a parent. These steps can be directed by the human subject's physician.

In preferred embodiments, the dose of a sodium salt is administered orally with at least six ounces, often at least eight ounces, of a beverage such as water or a water-based beverage, including sports drinks, soft drinks, juice, milk, or any other suitable beverage. Note that suitable beverages should not contain high amounts of carbohydrates. Typically, a suitable beverage would contain less than 10 g carbohydrates, preferably less than 5 g carbohydrates, and in some instances, zero carbohydrates. In some embodiments, the dose of sodium salt is contained in a packet, sachet, pouch, or other suitable single-dose container. In other embodiments, the sodium salt is provided in a drinkable form. In other embodiments, the dose of sodium salt is provided in a foodstuff, including for example a bar. In other embodiments, the dose of sodium salt is provided in a pill or capsule.

In some embodiments, the sodium salt comprises sodium citrate or sodium acetate, or a combination thereof. In some embodiments, the sodium salt includes multiple different sodium salts. In some embodiments, sodium chloride is one of the salts. In some embodiments, the sodium salt comprises sodium ascorbate. In some embodiments, other non-sodium salts are included, including but not limited to potassium salts. In some embodiments, all sodium salts are on the FDA Generally Recognized as Safe (GRAS) list. In some embodiments, one or more sodium salts are selected from the group consisting of sodium bicarbonate, sodium carbonate, sodium gluconate, sodium lactate, sodium phosphate, sodium carboxymethyl cellulose and sodium tartrate.

In some embodiments, it can be advantageous to combine at least three sodium salts, thereby reducing the dosage of any given counterion. For example, in one embodiment, a packet of sodium salts is provided for administration, wherein the packet contains a mixture of sodium ascorbate, sodium acetate, and sodium chloride. In some such embodiments, the amount of sodium provided by each of the sodium salts in the packet is at least 50 mg, or at least 100 mg.

As contemplated herein, the amount of sodium in the sodium salt administered to the person is between about 10 mg sodium per kg body weight of said subject and 100 mg sodium per kg body weight of said person. In some embodiments, a subject's serum sodium levels are tested prior to treatment for hyperglycemia by administering sodium salts at the concentration levels described herein.

In some embodiments, the salty taste of the sodium salt is masked with a suitable formulation. In some embodiments, artificial sweeteners or other flavorants are added. In some embodiments, miraculin is included in the formulation to mask the salty taste.

In some embodiments, an antiemetic agent is included in the formulation, including but not limited to natural products having antiemetic properties; e.g., ginger, cinnamon, and mint.

Advantages of the methods can include, but are not limited to, a reduction in the likelihood of death from hyperglycemic conditions, a reduction in hospitalizations arising from diabetic patients in a hyperglycemic state, a reduction in the time a diabetic person spends in a hyperglycemic state over the course of a day, a week, a month, or a year, a reduction in medical costs, a reduction in an individual's hemoglobin A1C percentage (A1C %), improvement in diabetes management, improvement in a person's health and well-being, reduced cumulative damage from hyperglycemia, a reduction in complications from retinopathy, kidney damage, neuropathy, or cardiovascular issues, and an increase in lifespans.

The methods of the disclosure are applicable to subtypes of Type 1 diabetes, as well as some other conditions that give rise to temporary hyperglycemic states, including but not limited to Type 2 diabetes mellitus (widely known as non-insulin dependent diabetes mellitus, NIDDM), Cushings Syndrome, Polycystic Ovarian Syndrome, hyperthyroidism, and hypothyroidism. While less likely to experience significant hyperglycemia as frequently as Type 1 diabetics, Type 2 diabetics also can benefit from the methods of the disclosure, and it can reduce incidence of diabetic ketoacidosis in Type 2 diabetics.

Compositions for reducing the duration of hyperglycemia and/or treating diabetes comprising one or more pharmaceutically acceptable salts of sodium, wherein the total concentration of sodium is between 250 mg and 5 g of sodium, irrespective of the weight of the anion component of said pharmaceutically acceptable salt of sodium, wherein said composition is formulated for oral delivery, wherein said composition comprises at least 250 mg of a sodium salt other than sodium chloride, and wherein said composition reduces the duration of hyperglycemia in a diabetic human being when administered to said human being in combination with insulin when said human being is hyperglycemic. In some embodiments, between 250 mg and 5000 mg of the sodium component of one or more sodium salts are provided in a suitable dosage form as described above, including as salts in a sealed packet to be added to and dissolved in a beverage for consumption. In some embodiments, these compositions are particularly useful for the treatment of Type 1 diabetes mellitus. In some embodiments, these compositions are pharmaceutical compositions suitable for an FDA-approved pharmaceutical product. In other embodiments, these compositions are dietary supplements.

BRIEF DESCRIPTION OF THE DRAWINGS

FIG. 1 is a graph showing average blood glucose levels of Type 1 diabetic subjects experiencing hyperglycemia as a function of time after initiation of either an experimental treatment in accordance with the methods described herein, or an active control treatment.

DETAILED DESCRIPTION

As used herein, each of the following terms has the meaning associated with it as described below.

The articles "a" and "an" are used herein to refer to one or to more than one (i.e. to at least one) of the grammatical object of the article. By way of example, "an element" means one element or more than one element.

As used herein, "plurality" means at least two.

As used herein, "FDA" means the United States Food and Drug Administration.

Any ranges cited herein are inclusive, e.g., "between about 50 mg and 100 mg" includes compositions of 50 mg and 100 mg.

As used herein, a human being, also referred to as a human subject, or as a subject, is "treated", or subjected to "treatment", when an earnest attempt is made to alleviate a medical disorder or disease. For example, a subject can be treated for a disorder by being administered a pharmacologic agent (e.g., a therapeutically effective amount of a sodium salt) that is intended to alleviate the disorder (e.g., hyperglycemia), irrespective of whether the treatment actually was successful in alleviating the disorder.

As used herein, a disease or disorder or medical affliction is "alleviated" if either the severity of a symptom of the disease or disorder or medical affliction, the frequency with which such a symptom is experienced by a subject, or both, are reduced.

A "subject" of diagnosis or treatment is a human.

A "therapeutic" treatment is a treatment administered to a subject who exhibits signs of pathology for the purpose of diminishing or eliminating those signs.

A "therapeutically effective amount" of a compound (or composition containing the compound) is that amount of compound (e.g., at least one sodium salt) which is sufficient to provide a beneficial effect to the subject (e.g., decreasing the blood glucose level of a hyperglycemic human being) to which the compound is administered.

A "dietary supplement" is an addition to the human diet, which is not a natural or conventional food, and which can be therapeutically effective when used according to the methods of the invention. Note that the dietary supplement can include ingredients which are conventionally used in food, including as preservatives, but the compositions as described are not natural or conventional foods.

Diabetes, also referred to as diabetes mellitus, is a chronic disease characterized by poor regulation of blood glucose in the body of a diabetic subject. People having Type 1 diabetes, referred to as "Type 1 diabetics", do not produce insulin (or make very little of it). People having Type 2 diabetes, referred to as "Type 2 diabetics", make insulin, but do not process it properly.

A "blood glucose level", alternatively referred to as a blood sugar level, is defined as the amount of glucose in a subject's blood, measured in mg/dL. A normal blood glucose level two hours after eating typically does not exceed 140 mg/dL. Hyperglycemia is defined herein as a blood glucose level greater than 180 mg/dL, and a hyperglycemic blood glucose level is one that is greater than 180 mg/dL. A "significantly hyperglycemic" blood glucose level is defined herein as a blood glucose level exceeding 250 mg/dL. Hypoglycemic is defined as a blood glucose level of less than 70 mg/dL.

An "antiemetic agent" is a compound that has been clinically demonstrated to reduce vomiting and/or nausea in subjects to which the antiemetic is administered. When diabetic patients are hyperglycemic, they often feel nauseous, and thus being administered an oral therapy can induce vomiting, or increase nausea. By administering an antiemetic agent in conjunction with the methods and compositions described herein, nausea and/or vomiting can be reduced in diabetic subjects. Some suitable antiemetics include natural compounds that have been demonstrated to have antiemetic properties, including but are not limited to ginger, lemon, cinnamon, and mint (including peppermint and spearmint).

The term "shorter-acting" insulin means an insulin having an onset of insulin effect within one hour of administration, and therefore includes insulins that are typically classified as either rapid-acting insulins or short-acting insulins. The term "longer-acting" insulin means an insulin having an onset of insulin effect of 60 minutes or more. Such longer-acting insulins typically have a duration of action of at least 12 hours, whereas shorter-acting insulins typically have a duration of action of less than 10 hours. Bolus insulins are almost always shorter-acting insulins.

This disclosure provides methods for lowering the blood sugar level in a hyperglycemic human being to below 180 g/dL (e.g., a therapeutically effective dose) by administering thereto a therapeutically effective amount of at least one sodium salt (e.g., a therapeutically effective dose). In some embodiments, the hyperglycemic human being is diabetic. In some embodiments, the human being has diabetes, is determined to be hyperglycemic, and is administered a dosage of a sodium salt composition that is effective, when combined with administration of insulin, in lowering the blood sugar level of the human being to below 180 g/dL (e.g., a therapeutically effective dose) within one hour or less. In some embodiments, the one or more sodium salts is administered to provide a dose of sodium between 10 mg sodium per kg and 100 mg sodium per kg body weight of said subject. The sodium salt composition can comprise a single type of sodium salt, or more than one type of sodium salt, including but not limited to two, three, four, five, six, seven, eight, nine, ten, or more different sodium salts, or potentially any number of sodium salts. In typical embodiments, one or more such sodium salts are on the FDA Generally Recognized as Safe (GRAS) list, and include, but are not limited to, sodium acetate, sodium citrate, sodium ascorbate, sodium chloride, sodium bicarbonate, sodium carbonate, sodium gluconate, sodium lactate, sodium phosphate, sodium carboxymethyl cellulose, and sodium tartrate. The sodium salt comprises the active pharmaceutical component, but the safety and efficacy are not independent of the anionic salt.

Too much of any compound can be problematic. While sodium cations are the active ingredient, it may be advantageous to have a balanced mix of anions, reducing concerns about toxicity of any single anion at higher dosages.

The amount of sodium in a given unit weight of a sodium salt depends on the counterion, as well as the extent of hydration. For example, the percent sodium content is higher for a given unit weight of sodium chloride than sodium citrate, while sodium citrate has a higher sodium content per unit weight than sodium ascorbate.

The counterions of the sodium salt can be important, both for positive or negative reasons. For example, sodium citrate is an anticoagulant, and too much sodium citrate could complicate treatment in some individuals. Too much sodium chloride can be problematic, and is widely contraindicated for treatment of diabetes (more broadly, too much sodium is also contraindicated for treatment of diabetes). Accordingly, while providing a sufficient dosage of sodium is important, not all sodium salt compositions having the same molar equivalents of sodium will have the same effect. For example, in human testing, we have found that inclusion of at least a modest amount of sodium chloride (in addition to one or more additional sodium salts) in the pharmaceutical composition can accelerate the return from hyperglycemic blood sugar levels to sub-hyperglycemic blood sugar levels or normal blood sugar levels. That said, pharmaceutical compositions having the same total sodium content, but lacking sodium chloride, also provide significant benefits and can reduce time in a hyperglycemic state. In some embodiments, a subject's serum sodium level and/or urine sodium level is tested prior to the commencement of the therapeutic approach described herein. In some embodiments, if a diabetic subject's serum sodium levels are above a specified level (e.g., 145 mEq/L), then the subject would be advised not to utilize the therapeutic approach described herein.

In some embodiments, at least 50%, or 60%, or 70%, or 80, or 90%, or 100% of the total sodium content of the sodium salts administered to a hyperglycemic human being according the methods of the disclosure are from a sodium salt other than sodium chloride. In some embodiments, at least 5 mg per kg body weight of the total sodium content of the sodium salts administered to a hyperglycemic human being according the methods of the disclosure are from a sodium salt other than sodium chloride, or at least 10 mg per kg, or at least 15 mg per kg, or at least 20 mg per kg body weight of the total sodium content of the sodium salts administered to a hyperglycemic human being according the methods of the disclosure are from a sodium salt other than sodium chloride. In some embodiments, at least 250 mg of a pharmaceutical composition administered to a hyperglycemic human being according the methods of the disclosure comprise a sodium salt other than sodium chloride, or at least 500 mg, or at least 750 mg, or at least 1 g, or at least 2 g, or at least 3 g.

One advantage of using sodium salts with anions that themselves are the conjugate base of a weak acid (e.g., the acetate ion is the conjugate base of acetic acid, a weak acid) is that diabetic ketoacidosis is characterized by an acidification of plasma, with falling arterial pH and reduced levels of bicarbonate buffer. While sodium chloride is a neutral salt, sodium salts such as sodium acetate, sodium citrate, sodium tartrate, and sodium ascorbate are alkalinizing agents that can neutralize excess acid in the blood. In some embodiments, when the pharmaceutical compositions described herein are dissolved in water, the pH is greater than 7.5, or greater than 8, or greater than 8.5.

In one embodiment, the sodium salt composition administered to a hyperglycemic human being (e.g., diabetic subject) comprises sodium acetate. In another embodiment, the sodium salt composition administered to a hyperglycemic human being (e.g., hyperglycemic diabetic subject) comprises sodium citrate. In another embodiment, the sodium salt composition administered to a hyperglycemic human being comprises sodium citrate and sodium chloride. In another embodiment, the sodium salt composition administered to a hyperglycemic human being (e.g., hyperglycemic diabetic subject) comprises sodium acetate and sodium chloride. In another embodiment, the sodium salt composition administered to a hyperglycemic human being (e.g., hyperglycemic diabetic subject) comprises sodium acetate and sodium citrate. In another embodiment, the sodium salt composition administered to a hyperglycemic human being (e.g., hyperglycemic diabetic subject) comprises sodium citrate, sodium acetate, and sodium chloride. In another embodiment, the sodium salt composition administered to a hyperglycemic human being comprises sodium ascorbate, sodium acetate, and sodium chloride. In some embodiments, a binary mixture of sodium salts includes sodium chloride. In some embodiments, a ternary mixture of sodium salts includes sodium chloride. In some embodiments, sodium chloride is not included as a sodium salt. In some embodiments, at least four different sodium salts are used.

In some embodiments, the sodium salt composition administered to a hyperglycemic human being (e.g., hyperglycemic diabetic subject) is a granular or powdered solid. In some such embodiments, the granular solid is packaged in single-use packaging. In some embodiments, the sodium salt composition administered to a hyperglycemic human being (e.g., hyperglycemic diabetic subject) is in the form of a foodstuff, including, for example, a chew, a bar, or an extruded edible. In preferred embodiments, the sodium salt composition administered to a hyperglycemic human being (e.g., hyperglycemic diabetic subject) is administered orally with at least six ounces of a beverage such as water or a water-based beverage, including sports drinks (ideally sugar-free), soft drinks, juice, milk, or any other suitable beverage containing less than 20 grams carbohydrates, preferably less than 10 g carbohydrates, optionally less than about 5 g carbohydrates or 0 g carbohydrates. In other embodiments, the sodium salt is provided in a drinkable form.

The sodium salt composition administered to a hyperglycemic human being (e.g., hyperglycemic diabetic subject) is administered at a dose of sodium between 10 mg sodium per kg and 100 mg sodium per kg body weight of said subject. This corresponds to roughly between 0.43 mmol sodium per kg and 4.3 mmol sodium per kg body weight of the diabetic subject.

Diabetics frequently are administered insulin, either as a basal insulin (e.g., Lantus®, a long-acting insulin available from Sanofi), as bolus insulin (e.g., Novolog®, a rapid-acting insulin available from Novo Nordisk), or both. The methods described herein work with any such regimen. In typical embodiments, a subject becomes aware of his/her hyperglycemic state, and can administer exogeneous insulin, typically a shorter-acting insulin. The insulin dosage administered in combination with the sodium salt can be any safe amount of insulin, and is typically the amount of insulin recommended for administration in the situation. Either the sodium salt or the insulin can be administered first, but they are administered within 30 minutes of each other, preferably within 15 minutes of each other, more preferably within five minutes of each other. When the sodium salt composition described herein is administered within 15 minutes of administration of insulin, they are defined as being administered "in combination" with each other.

When a hyperglycemic human being (e.g., hyperglycemic diabetic subject) uses the methods and pharmaceutical compositions described herein, benefits can include, but are not limited to, (i) improved quality of life, (ii) reduced costs, hospitalizations, and deaths associated with short-term complications such as diabetic ketoacidosis; and (iii) reduced long-term health complications that are prevalent in Type 1 diabetics, including but not limited to diabetic ketoacidosis, cardiovascular disease, nerve damage, kidney damage, retinopathy, and memory loss. When the methods of the disclosure are utilized, a diabetic subject can experience reduced time in a hyperglycemic state over the course of a day, a week, a month, or a year. This can yield a corresponding reduction in an individual's hemoglobin A1C %, which is a factor that is correlated with long-term health outcomes for diabetic subjects, as damage from hyperglycemia is widely believed to be, at least in part, cumulative.

The methods of the disclosure are applicable to subtypes of Type 1 diabetes, as well as some other conditions that give rise to temporary hyperglycemic states, including but not limited to Type 2 diabetes mellitus (widely known as non-insulin dependent diabetes mellitus, NIDDM), Cushings Syndrome, Polycystic Ovarian Syndrome, hyperthyroidism, and hypothyroidism. While less likely to experience significant hyperglycemia as frequently as Type 1 diabetics, Type 2 diabetics also can benefit from the methods of the disclosure, and it can be particularly helpful in preventing diabetic ketoacidosis on an acute basis in Type 2 diabetics.

In one embodiment, a Type 1 diabetic subject experiencing hyperglycemia eats a bar containing 6 grams of sodium acetate, 5 grams of sodium citrate, and 1.7 grams of sodium chloride. In some embodiments, the subject can also drink a non-sugary beverage and self-administer insulin.

In one embodiment, a Type 2 diabetic subject weighing 50 kg and experiencing significant hyperglycemia and early stage diabetic ketoacidosis consumes two gelatin capsules with a cup of water, and then self-administers insulin. In some embodiments, each capsule can contain a mixture of one (1) gram sodium acetate and one (1) gram sodium chloride.

In one embodiment, a Type 1 diabetic subject with a blood glucose level of 240 mg/dL can be administered insulin, and can then consume sodium acetate dissolved in a cup of water at a dosage equivalent to 20 mg sodium per kg body weight. The subject can be male or female.

In one embodiment, a Type 1 diabetic subject with a blood glucose level of 400 mg/dL is administered insulin, and then consumes sodium acetate dissolved in a cup of water at a dosage equivalent to 20 mg sodium per kg body weight. If the subject's blood glucose level does not drop to sub-hyperglycemic levels within 75 minutes, the subject can take additional sodium acetate dissolved in a cup of water at a dosage equivalent to 20 mg sodium per kg body weight.

In one embodiment, a Type 1 diabetic subject with a blood glucose level of 400 mg/dL is administered a shorter-acting insulin, and then consumes sodium acetate dissolved in a cup of a water-based beverage at a dosage equivalent to 20 mg sodium per kg body weight. The sodium acetate is administered within 15 minutes, preferably within 10 minutes, preferably within five minutes of administration of the shorter-acting insulin.

In some embodiments, the methods described herein can be used to treat or prevent ketoacidosis. In one embodiment, a hyperglycemic Type 1 diabetic subject tests the subject's own urine, and discovers a high level of ketones. The subject then self-administers bolus insulin, along with at least 6 ounces of a water-based beverage, and a combination of sodium acetate and sodium citrate at a dose equivalent to 10 mg sodium per kg body weight and 100 mg sodium per kg body weight of the subject.

In some embodiments, a physician directs a diabetic subject regarding how and when the methods of the disclosure should be utilized. In other embodiments, a diabetic subject makes those decisions.

In order to mask the salty taste of the active ingredients, one or more ingredients can be added to mask the flavor. This is particularly useful when the sodium salt composition is added to a beverage such as water, or eaten as a foodstuff. For example, miracle berry powder, or miraculin, can be utilized. In addition to standard flavors and additives, compounds known in the prior art as sour blockers, bitter blockers, or salt blockers can be added.

Formulation of Compositions

Compositions contemplated by the methods and compositions of the disclosure may be formulated and administered to a subject for treatment of the diseases or afflictions disclosed herein as described below, and/or as may be otherwise available to those of ordinary skill in the art.

The disclosure encompasses the preparation and use of sodium salt compositions, including both pharmaceutical compositions and dietary supplements, as an active ingredient useful for treatment of the diseases and disorders disclosed herein, including improving treatment of such diseases and disorders compared to the current state-of-the-art. Such a composition may consist of the active ingredient(s) alone, in a form suitable for administration to a subject, or the composition may comprise the active ingredient and one or more pharmaceutically acceptable carriers, one or more additional ingredients, or some combination of these. The active ingredient may be present in the composition in the form of a physiologically acceptable ester or salt, such as in combination with a physiologically acceptable cation or anion, as is well known in the art.

Note that a composition useful as a pharmaceutical composition could be identical to a dietary supplement composition. However, those classes of products are regulated differently in the United States.

The compounds of the disclosure are useful when formulated as salts. Examples of pharmaceutically acceptable salts are sodium salts formed with acids which form a physiological acceptable anion, for example, gluconate, acetate, citrate, malonate, tartrate, succinate, benzoate, carboxymethyl cellusose, ascorbate, α-ketoglutarate, and α-glycerophosphate. Suitable inorganic sodium salts may also be used, including but not limited to chloride, sulfate, nitrate, bicarbonate, and carbonate salts. Other physiological acceptable anions can also be suitable, as may be determined by those of ordinary skill in the art. Pharmaceutically acceptable salts may be obtained using standard procedures well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the composition, and which is not significantly deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

The descriptions of pharmaceutical compositions provided herein are directed to pharmaceutical compositions which are suitable for ethical administration to humans.

Pharmaceutical compositions that are useful in the methods of the disclosure may be prepared, packaged, or sold in formulations suitable for oral administration. In preferred embodiments, the pharmaceutical compositions are in formulations suitable for oral administration. Given the amount of sodium salts needed to accomplish the objective of reducing hyperglycemia significantly and rapidly, coupled with ease of patient compliance, methods of administration other than oral administration are inferior.

A pharmaceutical composition of the disclosure may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a composition of the disclosure will vary, depending upon the identity, size, and condition of the subject treated and further depending upon the route by which the composition is to be administered. By way of example, the composition may comprise between 1% and 100% (w/w) active ingredient.

A formulation of a pharmaceutical composition of the disclosure suitable for oral administration may be prepared, packaged, or sold in the form of a discrete solid dose unit including, but not limited to, a tablet, a hard or soft capsule, a cachet, a troche, a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation (or mixture thereof), optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and U.S. Pat. No. 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a composition of the disclosure which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropyl methylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the disclosure may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a composition of the disclosure may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of a dispersing or wetting agent, a suspending agent, and a preservative. Additional excipients, such as fillers and sweetening, flavoring, or coloring agents, may also be included in these formulations. As described herein, a "granular" formulation includes a "powdered" formulation.

A pharmaceutical composition of the disclosure may also be prepared, packaged, or sold in the form of an emulsion, such as an oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the disclosure are known in the art and described, for example in Genaro, ed., 1985, *Remington's Pharmaceutical Sciences*, Mack Publishing Co., Easton, Pa., which is incorporated herein by reference.

Dosage

For treatment of Type 1 diabetes, and complications thereof such as hyperglycemia, or other conditions leading to hyperglycemia, the dosage of sodium salts in the composition can be between about 250 mg and about 20 g when administered to adult subjects. More specifically, the dosage of sodium (not including its counterion such as acetate or citrate) is between about 100 mg and 8 g, preferably between about 250 mg and 5 g. The therapeutically effective dose of the pharmacologic agent can be administered using any medically acceptable mode of administration. Although the skilled artisan would contemplate any of the modes of administration known to one of ordinary skill, preferably the pharmacologic agent is administered according to the recommended mode of administration, for example, the mode of administration listed on the package insert of a commercially available agent.

In one embodiment, a mixture of 300 g of sodium acetate, 75 g of lactose and 100 g of talc can be combined, mixed, wetted with a sufficient quantity of alcohol and granulated followed by drying. The obtained granulate can be filled into capsules containing, for example, 1 g sodium acetate. The compositions can be useful, for example, for reducing hyperglycemia, reducing the risk of ketoacidosis, and/or treating Type 1 diabetes.

In one embodiment, 2 g sodium acetate and 2.5 g sodium citrate can be combined with a sweetening agent, a salt-masking agent, a colorant, and a flavoring agent in a tearable packet for administration, in combination with a beverage such as water, to a Type 1 diabetic experiencing hyperglycemia.

In one embodiment, a pharmaceutical composition comprises 0.5 g sodium from sodium acetate (either from anhydrous sodium acetate or hydrated sodium acetate, such as sodium acetate trihydrate), 0.5 g sodium from sodium citrate (anhydrous or hydrated), and 0.25 g sodium from sodium chloride, along with optional additives. This pharmaceutical composition contains 1.25 g sodium, and is suitable for administration according to the methods of the disclosure to an individual experiencing hyperglycemia, wherein the individual weighs between 12.5 kg and 125 kg.

In one embodiment, a pharmaceutical composition comprises 3 g sodium from sodium acetate (either from anhydrous sodium acetate or hydrated sodium acetate, such as sodium acetate trihydrate), along with optional additives. This pharmaceutical composition contains 3 g sodium, and is suitable for administration according to the methods of the disclosure to an individual experiencing hyperglycemia, wherein the individual weighs between 30 kg and 300 kg.

In one embodiment, a pharmaceutical composition comprises 0.5 g sodium from sodium ascorbate and 0.5 g sodium from sodium chloride, along with optional additives. This pharmaceutical composition contains 1 g sodium (and more than one gram chloride and ascorbate counterions), and is suitable for administration according to the methods of the disclosure to an individual experiencing hyperglycemia, wherein the individual weighs between 10 kg and 100 kg.

In one embodiment, a pharmaceutical composition comprises 2 g sodium from sodium acetate (either from anhydrous sodium acetate or hydrated sodium acetate, such as sodium acetate trihydrate), 0.1 g sodium from sodium chloride, along with optional additives. This pharmaceutical composition contains 2.1 g sodium, and is suitable for administration according to the methods of the disclosure to an individual experiencing hyperglycemia, wherein the individual weighs between 21 kg and 210 kg. In some optional embodiments, wherein the dosage of sodium is between 20 mg sodium per kg body weight of the subject and 60 mg sodium per kg body weight of the subject, this pharmaceutical composition would be useful for reducing the duration of hyperglycemia in a Type 1 diabetic weighing between 42 kg and 126 kg.

In one example, a dietary supplement comprises 1 g sodium from sodium citrate, 1 g sodium from sodium acetate, 1 g sodium from sodium ascorbate, and 0.25 g sodium from sodium chloride. This dietary supplement can be administered, in combination with insulin, to a hyperglycemic human being afflicted with diabetes, and the duration of hyperglycemia can be reduced significantly.

Timing and Frequency of Dosage

According to the methods described herein, a high-sodium salt composition is initially administered to a human subject after the subject tests positive for hyperglycemia. The threshold for administration of the sodium salt compositions of the disclosure can vary based on the subject, time of day, quantity of insulin recently administered, or other variables. In some embodiments, the composition is administered only if the subject is significantly hyperglycemic, or only when blood glucose levels exceed a certain value determined by the human subject and/or a physician and/or a drug label.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein the therapeutically effective dose comprises at least two doses of a sodium salt, optionally wherein the doses are separated by about 45 minutes.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein the therapeutically effective dose is between about 5 and about 100, optionally about 10 to about 80, or optionally about 20 to about 60, mg sodium per kg body weight of the human being.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, further comprising administering to the hyperglycemic human being at least one dose of shorter-acting insulin, optionally before administering the at least one dose of therapeutically effective dose of the sodium salt.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein at least one sodium salt other than sodium chloride is administered at a dose of greater than about 5 mg sodium per kg body weight of said subject.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, further comprising, prior to administering the therapeutically effective dose of the sodium salt, determining the blood glucose level of the hyperglycemic human being.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein the blood glucose level of the hyperglycemic human being is greater than 180 mg/dL, and/or the sub-hyperglycemic level is less than 180 mg/dL, and optionally more than 70 mg/dL.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein the method is for reducing the duration of hyperglycemia and comprises the steps of: (i) testing the blood glucose level of a human being to determine if the blood glucose level is hyperglycemic; and, (ii) if said testing indicates that said blood glucose level is hyperglycemic, administering to said subject both a dose of insulin and a therapeutically effective dose of a sodium salt such that said blood glucose level drops to sub-hyperglycemic levels within 75 minutes of administering said sodium salt, wherein said therapeutically effective dose is between 10 mg sodium per kg body weight of said subject and 100 mg sodium per kg body weight of said human being; wherein said therapeutically effective dose is administered to the human being orally; and, wherein optionally, at least one sodium salt other than sodium chloride is administered to the human being at a dose between 5 mg and 100 mg sodium per kg body weight of said subject.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein said human being is hyperglycemic due to a condition selected from the group consisting of Type 1 diabetes, Type 2 diabetes mellitus, Cushing's Syndrome, Polycystic Ovarian Syndrome, hyperthyroidism, and hypothyroidism.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein said human being has diabetes, optionally Type 1 diabetes.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein said method is a method for decreasing hemoglobin A1C levels in the blood of the human being, and/or said method is a method for treating and/or reducing the risk of developing ketoacidosis.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein testing said blood glucose level and administering said sufficient dose of a sodium salt are performed by said subject.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein the therapeutically effective dose is administered orally with and/or within at least six ounces, optionally at least eight ounces, of water or a water-based beverage, optionally wherein said water-based beverage comprises less than about 10 g, optionally less than about 5 g, or 0 g, carbohydrates.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein the therapeutically effective dose is a solid, optionally in a packaged granular formulation, which, upon addition to a drinkable water-based beverage, dissolves in said drinkable water-based beverage.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein said therapeutically effective dose is in an oral dosage form selected from the group consisting of a pill, a tablet, a lozenge, a bar, and a granular formulation; optionally wherein said dosage form comprises or is administered with a sweetener or flavorant; and/or optionally wherein said dosage form further comprises and/or is administered with an antiemetic agent.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein said sodium salt comprises sodium and a physiological acceptable anion, optionally selected from the group consisting of carboxymethyl cellulose, acetate, citrate, malonate, tartrate, succinate, benzoate, ascorbate, α-ketoglutarate, α-glycerophosphate, chloride, sulfate, nitrate, bicarbonate, and carbonate.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein the therapeutically effective dose comprises at least one, at least two, or at least three of sodium acetate, sodium citrate, sodium ascorbate, sodium chloride, sodium carboxymethyl cellulose, sodium bicarbonate, sodium carbonate, sodium gluconate, sodium lactate, sodium phosphate, and sodium tartrate, and/or combinations thereof; sodium citrate and sodium chloride, sodium acetate, sodium ascorbate, and sodium chloride; or, sodium acetate and sodium citrate.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein said sodium salt is not sodium chloride.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein more than one different sodium salt is used, wherein one of said sodium salts is sodium chloride that is administered to said subject at a dose greater than about 5 mg and less than about 100 mg sodium chloride per kg body weight of said subject, and said sodium chloride comprises less than 50% by weight of the total dosage of sodium salts in the therapeutically effective dose.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein said dose of sodium salt is drinkable, in the form of a foodstuff, and/or contained within a pill, tablet or capsule.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein the steps of testing said blood glucose level and administering said sufficient dose of a sodium salt are performed at least three times within a three-month period.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein the therapeutically effective dose is administered to the hyperglycemic human being multiple times within a year, three months, one month, a week, or even a day; not more than ten times in a week; or at least any of three, six, ten, 20, or 30 times within a three-month period.

In an embodiment, a method is described comprising administering to a hyperglycemic human being at least one dose of therapeutically effective dose of at least one sodium salt, wherein the blood glucose level of said human being decreases to a sub-hyperglycemic level within about 75 minutes, optionally within about 60 or about 45 minutes, of said administering, wherein the therapeutically effective dose is administered only if the blood glucose level of the hyperglycemic human being is significantly hyperglycemic, i.e., greater than 250 mg/dL.

In an embodiment, a composition is contemplated for decreasing the blood glucose level of a hyperglycemic human being to sub-hyperglycemic levels within about 75 minutes of administering said composition to the hyperglycemic human being, for managing hemoglobin A1C levels of a diabetic patient, for reducing the likelihood of ketoacidosis, and/or for treatment of Type 1 diabetes and/or complications associated therewith, said composition comprising at least one therapeutically effective dose of between about 250 mg and about 20 g, optionally about 500 mg and about 5000 mg, of at least one pharmaceutically acceptable salt of sodium, including at least about 250 mg of a sodium salt other than sodium chloride, formulated for oral delivery.

In an embodiment, a pharmaceutical composition is contemplated for decreasing the blood glucose level of a hyperglycemic human being to sub-hyperglycemic levels within about 75 minutes of administering said pharmaceutical composition to the hyperglycemic human being, for managing hemoglobin A1C levels of a diabetic patient, and/or for treatment of Type 1 diabetes and/or complications associated therewith, said pharmaceutical composition comprising at least one therapeutically effective dose of between about 250 mg and about 20 g, optionally about 500 mg and about 5000 mg, of at least one pharmaceutically acceptable salt of sodium, including at least about 250 mg of a sodium salt other than sodium chloride, formulated for oral delivery, wherein said composition is a granular solid.

In an embodiment, a pharmaceutical composition is contemplated for decreasing the blood glucose level of a hyperglycemic human being to sub-hyperglycemic levels within about 75 minutes of administering said pharmaceutical composition to the hyperglycemic human being, for managing hemoglobin A1C levels of a diabetic patient, and/or for treatment of Type 1 diabetes and/or complications associated therewith, said pharmaceutical composition comprising at least one therapeutically effective dose of between about 250 mg and about 20 g, optionally about 500 mg and about 5000 mg, of at least one pharmaceutically acceptable salt of sodium, including at least about 250 mg of a sodium salt other than sodium chloride, formulated for oral delivery, wherein said sodium salt other than sodium chloride is selected from the group consisting of sodium acetate, sodium citrate, sodium ascorbate, and combinations thereof.

In an embodiment, an article of manufacture comprises at least one unit dose comprising the pharmaceutical compositions described above, optionally wherein said article of manufacture is a tablet, hard capsule, soft capsule, cachet, troche, lozenge, powder, or granular formulation, aqueous suspension or solution, oily suspension or solution, and/or an emulsion.

In some embodiments, use of a pharmaceutical composition as described above, or the article of manufacture described above, in the preparation of a medicament for decreasing the blood glucose level of a hyperglycemic human being to sub-hyperglycemic levels within about 75 minutes of administering said pharmaceutical composition to the hyperglycemic human being, for managing hemoglobin A1C levels of a diabetic patient, and/or treatment of Type 1 diabetes and/or complications associated therewith In an embodiment, a kit comprises a pharmaceutical composition as described above and/or at least one article of manufacture as described above, optionally contained within a single-dose container; and, instructions for use for decreasing the blood glucose level of a hyperglycemic human being to sub-hyperglycemic levels within about 75 minutes of administering said pharmaceutical composition to the hyperglycemic human being, for managing hemoglobin A1C percentages of a diabetic patient, and/or treatment of Type 1 diabetes and/or complications associated therewith.

In an embodiment, a kit comprises a pharmaceutical composition as described above and/or at least one article of manufacture as described above, optionally contained within a single-dose container; and, instructions for use for decreasing the blood glucose level of a hyperglycemic human being to sub-hyperglycemic levels within about 75 minutes of administering said pharmaceutical composition to the hyperglycemic human being, for managing hemoglobin A1C percentages of a diabetic patient, and/or treatment of Type 1 diabetes and/or complications associated therewith, wherein said instructions for use describe administering to a hyperglycemic human being a therapeutically effective dose of a sodium salt, wherein the blood glucose level of said human being decreases to sub-hyperglycemic levels within about 75 minutes of said administering; and/or, testing the blood glucose level of a human being to determine if the blood glucose level is hyperglycemic and if said testing indicates that said blood glucose level is hyperglycemic administering to said subject both a dose of shorter-acting insulin and a therapeutically effective dose of a sodium salt such that said blood glucose level drops to sub-hyperglycemic levels within 75 minutes of administering said sodium salt wherein said therapeutically effective dose is between 10 mg sodium per kg body weight of said subject and 100 mg sodium per kg body weight of said human being, said therapeutically effective dose is administered to the human being orally, and, optionally, at least one sodium salt other than sodium chloride is administered to the human being at a dose of greater than 10 mg sodium per kg body weight of said subject.

In an embodiment, a method for managing hemoglobin A1C levels in a diabetic human subject which comprises the following steps:
  A. testing the blood glucose level of a human subject to determine if the subject's blood glucose level is hyperglycemic; and
  B. if said testing indicates that said subject's blood glucose level is hyperglycemic, administering to said subject a dose of insulin and a sufficient dose of a sodium salt such that said subject's blood glucose level drops to sub-hyperglycemic levels within 75 minutes of administering said sodium salt,
wherein said sodium salt is administered at a dose of sodium between 10 mg sodium per kg body weight of said subject and 100 mg sodium per kg body weight of said subject, wherein said dose of said sodium salt is administered orally, wherein at least one sodium salt other than sodium chloride is administered at a dose of greater than 5 mg sodium per kg body weight of said subject, and wherein said sequential steps of testing said blood glucose level and administering said sufficient dose of a sodium salt are performed at least three times within a three-month period.

EXAMPLES

The disclosure is now described with reference to the following examples. These examples are provided for the purpose of illustration only and the disclosure should in no way be construed as being limited to these examples but rather should be construed to encompass any and all variations which become evident as a result of the teaching provided herein.

Example 1

An open-label pilot clinical study was conducted with two male Type 1 diabetic subjects. When the subjects were significantly hyperglycemic, they self-medicated by following either the active control procedure or the experimental procedure as described herein. Neither subject exclusively followed one of the treatment conditions; instead, sometimes a subject followed the active control procedure and other times the subject followed the experimental treatment procedure.

For the active control, the significantly hyperglycemic Type 1 subject consumed eight ounces of water, took insulin as appropriate in accordance with their habits and insulin pump recommendation, and waited until their blood glucose levels were no longer hyperglycemic. This is the current standard practice treatment among Type 1 diabetics. Blood glucose levels were recorded at the outset and every 15 minutes after the intervention was commenced until blood glucose levels dropped to less than 180 mg/dL.

For the experimental treatment tests, the significantly hyperglycemic subject consumed at least eight ounces of water along with a therapeutic dosage of one or more sodium salts administered at a dose of sodium between 20 mg sodium per kg body weight of said subject and 60 mg sodium per kg body weight of said subject, took insulin as appropriate in accordance with their habits and pump recommendation, and waited until their blood glucose levels were no longer hyperglycemic. The therapeutic dosage of sodium salts could be administered prior to, or after, the insulin administration. Typically, the dosage of sodium salts was administered within five minutes of the insulin administration. Blood glucose levels were recorded at the outset and every 15 minutes after the intervention was commenced until blood glucose levels dropped to less than 180 mg/dL. Sodium salts included sodium chloride, sodium citrate, sodium acetate, sodium ascorbate, and combinations thereof.

The average blood glucose levels for the active control procedures and experimental treatment procedures are provided in the graph shown in FIG. 1. The average starting blood glucose levels were approximately 320 mg/dL for the two groups.

Clearly, when treated with the experimental procedure, subjects (on average, over 16 tests) experienced reduced duration and magnitude of hyperglycemic events. On average, hyperglycemic blood glucose levels were dropped below hyperglycemic levels in roughly 50 minutes when the Type 1 diabetics were subjected to the experimental treatment procedure. In contrast, when subjected to the active control procedure, it took an average of roughly 160 minutes to return to sub-hyperglycemic blood glucose levels of less than 180 mg/dL. Accordingly, when subjected to the active control treatment, which is the long-time standard of care for diabetic individuals, the hyperglycemic period was over three times longer than when individuals self-administered the experimental treatment procedure. This is an enormous difference, particularly given (i) the discomfort associated with hyperglycemia, (ii) the risk of ketoacidosis when high levels of hyperglycemia persist for long periods, and (iii) that the duration and magnitude of hyperglycemic events is believed to correlate closely with A1C levels, which correlate with long-term complications of diabetes.

Example 2

A six-month study was conducted with an adult male Type 1 diabetic subject weighing roughly 85 kg. When the subject's blood glucose level was greater than 200 mg/dL and the subject was aware of the hyperglycemia and had access to the experimental sodium compositions described herein, the subject regularly self-administered at least eight ounces of water along with a therapeutic dosage of one or more sodium salts administered at a dose of sodium between 10 mg sodium per kg body weight of said subject and 100 mg sodium per kg body weight of said subject, and took insulin if appropriate in accordance with his habits and pump recommendation. During this period, the subject was not hospitalized for any diabetic ketoacidosis events. The subject's hemoglobin A1C percentage was tested prior to commencement of the study and was 7.6. After the 6-month study, the subject's A1C percentage dropped to 7.2.

Example 3

In one embodiment, an adult male Type 1 diabetic subject experiencing significant hyperglycemia was administered five units of bolus insulin, then was administered a composition comprising inactive ingredients, approximately 10 grams of sodium citrate, and approximately 1.7 g sodium chloride. The composition was dissolved in 8 ounces of water, and consumed by the subject. In less than 45 minutes, the subject's blood glucose level dropped below sub-hyperglycemic levels.

Example 4

In one embodiment, an adult male Type 1 diabetic subject experiencing significant hyperglycemia was administered five units of a shorter-acting insulin, then was administered a composition comprising inactive ingredients, approximately 4 grams of sodium acetate trihydrate, approximately 4 grams of sodium ascorbate, and approximately 1.7 g sodium chloride. The composition was dissolved in 8 ounces of water, and consumed by the subject. In less than 45 minutes, the subject's blood glucose level dropped below sub-hyperglycemic levels.

Example 5

In one embodiment, an adult male Type 1 diabetic subject experiencing significant hyperglycemia was administered five units of shorter-acting insulin, then was administered a composition comprising inactive ingredients, approximately 10 grams of sodium citrate, and approximately 0.8 g sodium chloride. The composition was dissolved in approximately one pint of water, and consumed by the subject. In less than 60 minutes, the subject's blood glucose level dropped below sub-hyperglycemic levels.

Example 6

In one embodiment, an adult male Type 1 diabetic subject experiencing significant hyperglycemia was administered four units of bolus insulin, then was administered a pharmaceutical composition comprising inactive ingredients, approximately 10 grams of sodium citrate, and approximately 3.5 g sodium chloride. The pharmaceutical composition was dissolved in approximately one pint of water, and consumed by the subject. In less than 45 minutes, the subject's blood glucose level dropped below sub-hyperglycemic levels.

Example 7

In one embodiment, an adult male Type 1 diabetic subject experiencing significant hyperglycemia was administered 3.5 units of bolus insulin, then was administered a composition comprising inactive ingredients, approximately 3.8 grams of sodium acetate trihydrate, approximately 5 grams of sodium citrate, and approximately 1.7 g sodium chloride. The composition was dissolved in 8 ounces of water, and consumed by the subject. In less than 60 minutes, the subject's blood glucose level dropped below sub-hyperglycemic levels.

Example 8

In one embodiment, an adult male Type 1 diabetic subject experiencing significant hyperglycemia was administered insulin as recommended by his insulin pump, then was administered a composition comprising inactive ingredients and approximately 15 grams of sodium citrate. The composition was dissolved in 8 ounces of water, and consumed by the subject. In less than 75 minutes, the subject's blood glucose level dropped below sub-hyperglycemic levels.

Example 9

In one embodiment, a Type 1 diabetic subject experiencing significant hyperglycemia was administered insulin as recommended by his insulin pump, then was administered a composition comprising inactive ingredients and approximately 8 grams of sodium acetate trihydrate. The composition was dissolved in 8 ounces of water, and consumed by the subject. In less than 75 minutes, the subject's blood glucose level dropped below sub-hyperglycemic levels.

Example 10

In one embodiment, a Type 1 diabetic subject (weighing between 175 and 200 pounds) experiencing significant hyperglycemia (a blood sugar level of 499 mg/dL) was administered eight units of insulin, then was administered a pharmaceutical composition comprising inactive ingredients and approximately 7 grams of sodium acetate trihydrate. The pharmaceutical composition was dissolved in 8 ounces of water, and consumed by the subject. After 45 minutes, the subject's blood glucose level dropped to 306 mg/dL, and the subject self-administered another approximately 2 g of sodium acetate trihydrate. After another 45 minutes, the subject's blood glucose level had fallen below sub-hyperglycemic levels.

Example 11

In one embodiment, a Type 1 diabetic subject experiencing significant hyperglycemia was administered three units of insulin as recommended by his insulin pump, then was administered a dietary supplement comprising inactive ingredients and approximately 10 grams of sodium bicarbonate and approximately 2 grams of sodium chloride. The dietary supplement was dissolved in 8 ounces of water, and consumed by the subject. In less than 30 minutes, the subject's blood glucose level dropped below sub-hyperglycemic levels.

Example 12

In one embodiment, a Type 1 diabetic subject experiencing significant hyperglycemia (blood glucose level of 330 mg/dL) was administered four units of insulin as recommended by his insulin pump, then was administered a pharmaceutical composition comprising inactive ingredients and approximately 10 grams of sodium carboxymethyl cellulose and approximately 2 grams of sodium chloride. The pharmaceutical composition was suspended in 8 ounces of water, and consumed by the subject. In less than 75 minutes, the subject's blood glucose level dropped below sub-hyperglycemic levels. The blood sugar level remained unusually stable for four hours thereafter.

Example 13

In one embodiment, a Type 1 diabetic subject who had not received basal insulin for roughly four hours, and was experiencing significant hyperglycemia (blood glucose level of 350 mg/dL), self-administered seven units of insulin, then self-administered a pharmaceutical composition comprising inactive ingredients, approximately 14 grams of sodium gluconate, and approximately 3 grams of sodium chloride. The pharmaceutical composition was dissolved in 8 ounces of water, and consumed by the subject. In one hour, the subject's blood glucose level dropped to 180 mg/dL, and further dropped to 140 mg/dL after 75 minutes.

Example 14

In one embodiment, a Type 1 diabetic subject (weighing between 200 and 220 pounds) experiencing significant hyperglycemia (a blood sugar level of 300 mg/dL) was administered eight units of insulin, then waited 30 minutes until his blood sugar level was 266 mg/dL. At that point, the individual self-administered a pharmaceutical composition comprising inactive ingredients and approximately 3 grams of sodium from a composition comprising sodium citrate, sodium chloride, and sodium ascorbate. The composition was dissolved in a glass of water, and consumed by the subject. After 30 additional minutes, the subject's blood glucose level dropped to 174 mg/dL.

Example 15

A four-month study was conducted with an adult male Type 1 diabetic subject. When the subject's blood glucose level was greater than 250 mg/dL and the subject was aware of the hyperglycemia and had access to the experimental sodium compositions described herein, the subject regularly self-administered at least eight ounces of water along with a therapeutic dosage of one or more sodium salts administered at a dose of sodium between 10 mg sodium per kg body weight of said subject and 100 mg sodium per kg body weight of said subject, and took insulin if appropriate in accordance with his habits and insulin pump recommendation. During this period, the subject was not hospitalized for any diabetic ketoacidosis events. The subject's hemoglobin A1C percentage was tested prior to commencement of the study and was 7.6. After the 4-month study, the subject's A1C percentage dropped to 7.3.

INCORPORATION BY REFERENCE

All publications, patents, and patent applications cited herein are hereby expressly incorporated by reference in their entirety and for all purposes to the same extent as if each was so individually denoted.

EQUIVALENTS

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

We claim:
1. A method for reducing the duration of hyperglycemia which comprises the following steps:
   A. testing the starting blood glucose level of a human subject to determine if the subject's blood glucose level is hyperglycemic; and

B. if said testing indicates that said subject's starting blood glucose level is hyperglycemic, administering to said subject both a dose of insulin and a sufficient dose of a sodium salt such that said subject's blood glucose level drops to sub-hyperglycemic levels within 75 minutes of administering said sodium salt, wherein said sodium salt is administered at a dose of sodium between 10 mg sodium per kg body weight of said subject and 100 mg sodium per kg body weight of said subject, wherein said dose of said sodium salt is administered orally, and wherein at least one sodium salt other than sodium chloride is administered at a dose of greater than 5 mg sodium per kg body weight of said subject.

2. The method of claim 1, wherein said human subject has diabetes.

3. The method of claim 2, wherein said human subject has Type 1 diabetes.

4. The method of claim 1, wherein said steps of testing said starting blood glucose level and administering said sufficient dose of a sodium salt are performed by said subject.

5. The method of claim 1, wherein said sufficient dose of a sodium salt is co-administered with at least 6 ounces of a beverage.

6. The method of claim 1, wherein said sufficient dose of a sodium salt is administered orally in a dosage form selected from the group consisting of a pill, a tablet, a lozenge, a bar, and a granular formulation.

7. The method of claim 1, wherein said sufficient dose of said sodium salt is provided in a packaged granular formulation which, upon addition to a drinkable water-based beverage, dissolves in said drinkable water-based beverage.

8. The method of claim 1, wherein said sodium salt that is administered at said sufficient dose is selected from the group consisting of sodium acetate, sodium citrate, sodium ascorbate, sodium bicarbonate, sodium carbonate, sodium gluconate, sodium lactate, sodium phosphate, sodium carboxymethyl cellulose and sodium tartrate, and combinations thereof.

9. The method of claim 1, wherein said sodium salt that is administered at said sufficient dose is selected from the group consisting of sodium acetate, sodium citrate, and combinations thereof.

10. The method of claim 1, wherein said sufficient dose of a sodium salt comprises at least two different sodium salts.

11. The method of claim 1, wherein said sufficient dose of a sodium salt does not comprise sodium chloride.

12. The method of claim 10, wherein one of said at least two different sodium salts is sodium chloride, wherein sodium chloride is administered to said subject at a dose greater than 5 mg sodium chloride per kg body weight of said subject and less than 100 mg sodium chloride per kg body weight of said subject, and wherein said sodium chloride comprises less than 50% by weight of the total dosage of sodium salts.

13. The method of claim 1, wherein said sufficient dose of a sodium salt is administered in the form of a foodstuff.

14. The method of claim 1, wherein said sequential steps of testing said starting blood glucose level and administering said sufficient dose of a sodium salt are performed at least three times within a three month period.

15. The method of claim 1, wherein said sufficient dose of a sodium salt is administered to the hyperglycemic human being multiple times within a year, three months, one month, a week, or even a day; not more than ten times in a week; or at least any of three, six, ten, 20, or 30 times within a three-month period.

16. The method of claim 1, wherein an antiemetic agent is co-administered with said sufficient dose of a sodium salt.

17. The method of claim 1, wherein a sufficient dose of a sodium salt is administered only if said subject's starting blood glucose level is significantly hyperglycemic.

18. The method of claim 1, wherein a sufficient dose of a sodium salt is administered only if said subject's starting blood glucose level is greater than 250 mg/dL.

19. The method of claim 1, wherein a sufficient dose of a sodium salt is administered only if said subject's starting blood glucose level is greater than 300 mg/dL.

20. The method of claim 1, wherein said method reduces the likelihood of the subject requiring hospitalization for diabetic ketoacidosis.

21. The method of claim 1, wherein said sufficient dose of a sodium salt and said dose of insulin are both administered within a 15-minute time period.

* * * * *